(12) United States Patent
Bosquet et al.

(10) Patent No.: US 9,952,181 B2
(45) Date of Patent: Apr. 24, 2018

(54) DEVICE FOR THE AUTOMATED NON-DESTRUCTIVE TESTING OF STIFFENERS OF AN AIRCRAFT COMPOSITE STRUCTURE

(71) Applicant: EUROPEAN AERONAUTIC DEFENCE AND SPACE COMPANY EADS FRANCE, Paris (FR)

(72) Inventors: Catherine Bosquet, Sucé sur Erdre (FR); Bruno Thomas, Paris (FR); Louis Le Pinru, Rezé (FR)

(73) Assignee: AIRBUS, Blagnac (FR)

( * ) Notice: Subject to any disclaimer, the term of this patent is extended or adjusted under 35 U.S.C. 154(b) by 308 days.

(21) Appl. No.: 14/655,693

(22) PCT Filed: Dec. 9, 2013

(86) PCT No.: PCT/EP2013/075982
§ 371 (c)(1),
(2) Date: Jun. 25, 2015

(87) PCT Pub. No.: WO2014/102055
PCT Pub. Date: Jul. 3, 2014

(65) Prior Publication Data
US 2015/0346158 A1 Dec. 3, 2015

(30) Foreign Application Priority Data
Dec. 28, 2012 (FR) ...................... 12 62938

(51) Int. Cl.
*G01N 29/00* (2006.01)
*G01N 29/04* (2006.01)
(Continued)

(52) U.S. Cl.
CPC ......... *G01N 29/043* (2013.01); *G01N 29/226* (2013.01); *G01N 29/265* (2013.01);
(Continued)

(58) Field of Classification Search
CPC .................................................. G01N 29/265
See application file for complete search history.

(56) References Cited

U.S. PATENT DOCUMENTS

| 6,167,760 B1 | 1/2001 | Brunty et al. |
| 2006/0162456 A1* | 7/2006 | Kennedy ............. G01N 29/225 73/620 |

(Continued)

*Primary Examiner* — Paul West
*Assistant Examiner* — Mark A Shabman
(74) *Attorney, Agent, or Firm* — Im IP Law; C. Andrew Im

(57) ABSTRACT

A device for testing a stiffener of an aircraft structure made from composite materials. At least one ultrasound sensor is configured to provide measurements relative to a material health state of the stiffener. The device includes a protective enclosure for housing the ultrasound sensor and a mobile gantry configured to move along the stiffener. The protective enclosure with the ultrasound sensor is mounted inside the mobile gantry. A driver is configured to drive the mobile gantry along the stiffener. A clamper is rigidly connected to the protective enclosure and configured to hold the ultrasound sensor pressed against the surface of the stiffener to be controlled. A locator to synchronize each area of the surface of the stiffener with the measurement of the ultrasound sensor.

11 Claims, 3 Drawing Sheets

(51) Int. Cl.
*G01N 29/22* (2006.01)
*G01N 29/265* (2006.01)

(52) U.S. Cl.
CPC .............. *G01N 2291/0231* (2013.01); *G01N 2291/02827* (2013.01); *G01N 2291/2694* (2013.01)

(56) References Cited

U.S. PATENT DOCUMENTS

2006/0243051 A1* 11/2006 Bui ...................... G01N 29/043
    73/618
2008/0066553 A1* 3/2008 Espada Tejedor ... G01N 29/225
    73/627

* cited by examiner

DEVICE FOR THE AUTOMATED NON-DESTRUCTIVE TESTING OF STIFFENERS OF AN AIRCRAFT COMPOSITE STRUCTURE

RELATED APPLICATIONS

This application is a § 371 application from PCT/EP2013/075982 filed Dec. 9, 2013, which claims priority from French Patent Application No. 12 62938 filed Dec. 28, 2012, each of which is herein incorporated by reference in its entirety.

FIELD OF THE INVENTION

The invention relates to an automated non-destructive inspection device for inspecting the stiffeners of a structure made of self-stiffened composite materials of an aircraft. This device makes it possible to inspect the state of material health of a stiffener automatically even when the structure is closed or of small dimensions. This inspection is performed by means of an ultrasound sensor mounted on an embedded gantry.

The invention relates also to a system for inspecting stiffeners of structures made of composite materials comprising the device described previously intended to be embedded in the structure and remote display and control devices.

The invention is applicable in the field of aeronautics and, in particular, in the field of the inspection of aeronautical parts before construction of the aircraft or during maintenance.

BACKGROUND OF THE INVENTION

In the field of the inspection of aeronautical parts, and notably of stiffeners, it is known practice to use an ultrasound sensor to perform a manual non-destructive inspection of the state of material health of the stiffeners mounted on an aircraft structure. The sensor sends ultrasound signals toward the stiffener. These ultrasound signals are transmitted through said stiffener and reflected by the different interfaces passed through. The flight time and the amplitude of the ultrasound signal received give information on the material health of the part.

Generally, the ultrasound sensor is mounted at the end of a handle displaced manually by an operator. This ultrasound sensor is linked to a display screen which displays the image of the state of internal health of the stiffener as the ultrasound sensor is displaced. Thus, the image displayed on the screen scrolls as the operator displaces the ultrasound sensor along the stiffener.

Such an operation is generally restrictive because it requires great attention on the part of the operator who has to displace the ultrasound sensor while ensuring that the latter is indeed in contact with the surface of the stiffener and who must, at the same time, view the display screen to check the state of the inspected area of the stiffener. This operation requires the operator to be qualified, which results in a relatively high labor cost.

Furthermore, this method involves an inspection of the state of internal health of the stiffener, stiffener by stiffener. Given the number of stiffeners mounted on each aircraft structure, it will be understood that the complete inspection of all the stiffeners of a structure is lengthy and tedious.

Furthermore, since the operator has to be able to access the stiffener and follow the stiffener over its entire length, only open structures can be inspected, that is to say planar structures or structures that have easy accessibility for the operator. Thus, only panels of structures can be inspected. The closed structures, such as the caissons, for which there are only small lateral openings, cannot be inspected by the conventional method. Now, with the arrival on the market of aircraft produced largely in composite materials, more and more closed structures are manufactured in composite materials with stiffeners distributed over the internal wall of these structures.

There is therefore a real need for an automatic ultrasound inspection device which can be displaced independently along stiffeners of the structures made of composite materials, regardless of the form of the structure (closed or open).

OBJECT AND SUMMARY OF THE INVENTION

The aim of the invention is precisely to remedy this lack by proposing an automated ultrasound inspection device, that is displaced totally independently along stiffeners of a self-stiffened structure of composite materials. For this, the device of the invention comprises an ultrasound sensor mounted on a gantry suitable for being displaced along the stiffener while ensuring that the ultrasound sensor is pressed against the stiffener and transmitting an image of the material health of the stiffener to a remote image display device.

More specifically, the invention relates to a device for inspecting a stiffener of a structure made of composite materials of an aircraft, comprising at least one ultrasound sensor suitable for supplying measurements relating to a state of internal health of the stiffener. The state of internal health of a stiffener is the state of health of the material forming the stiffener, also called state of material health. This device is characterized by the fact that it comprises:
    an ultrasound sensor protection enclosure, in which said ultrasound sensor is housed,
    a mobile gantry suitable for being displaced along the stiffener and inside which is mounted the enclosure with the ultrasound sensor,
    driving means suitable for driving the gantry in displacement along the stiffener,
    gripping means, secured to the protection enclosure and suitable for keeping the ultrasound sensor pressed against the surface of the stiffener to be inspected,
    locating means for synchronizing each area of the surface of the stiffener with the measurement of the ultrasound sensor.

This device can comprise one or more of the following features:
    the gripping means comprise at least one pressure spring, a wall skid having a front face aligned with a front face of the ultrasound sensor and a rear face on which the spring bears, and at least one roller housed in the front face of the wall skid and suitable for rolling over the surface of the stiffener to ensure a mechanical contact between the wall skid and the stiffener;
    the protection enclosure comprises a water tank suitable for maintaining a film of water between the ultrasound sensor and the surface of the stiffener;
    the driving means comprise a motor linked to at least one driving wheel suitable for displacing the gantry;—the gantry is in the form of an inverted U comprising two lateral legs intended to be positioned on either side of the stiffener and a bridge linking the two lateral legs;
    the driving wheel is housed in a module secured to the gantry and forming a central leg of said gantry;

the module is situated facing the protection enclosure of the sensor, along a surface opposite the inspected surface of the stiffener;

the locating means comprise a coder suitable for determining a position of the ultrasound sensor as it is displaced;

it comprises end-of-trajectory detection means linked to the driving means to automatically stop the displacement of the gantry at the end of the stiffener;

the protection enclosure of the ultrasound sensor has a form which closely follows the form of the stiffener.

The invention relates also to a system for inspecting the state of internal health of a stiffener, comprising the inspection device described previously, linked to a display device suitable for displaying the measurements from the ultrasound sensor and to a control device.

DETAILED DESCRIPTION OF EMBODIMENTS OF THE INVENTION

The ultrasound inspection device of the invention is an automatic and standalone device that can be displaced along a stiffener without the presence of an operator. This inspection device is equipped with an ultrasound sensor of the same type as those used in the prior art. However, in the invention, the ultrasound sensor is mounted on a mobile gantry, suitable for being displaced along the stiffener and for keeping said ultrasound sensor constantly pressed against the stiffener.

Figure 1:
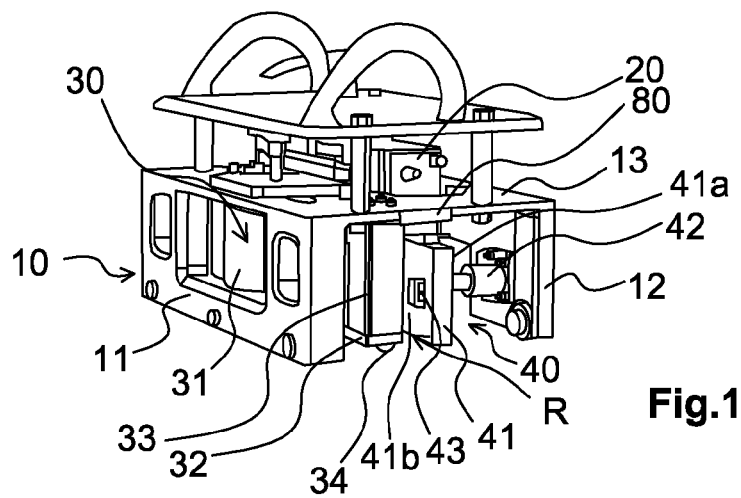
FIG. 1 represents a perspective view of the ultrasound inspection device according to the invention.
Figure 2:
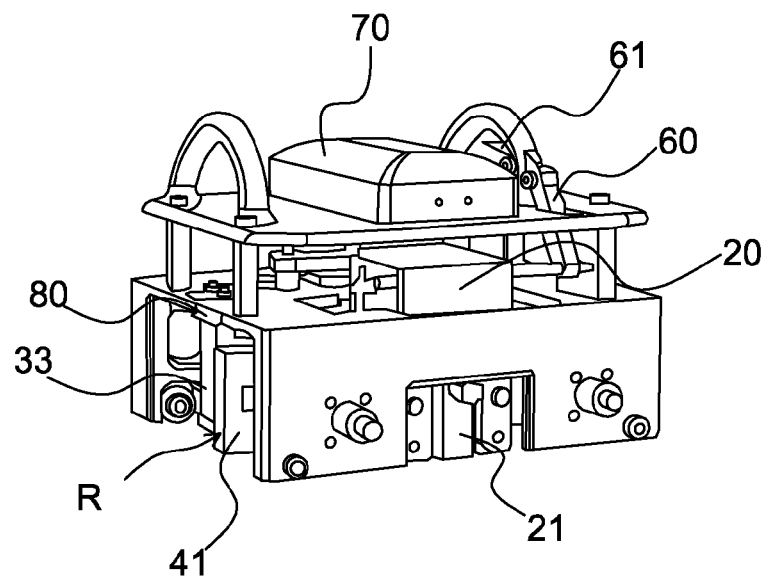
FIG. 2 represents a side view of the ultrasound inspection device according to the invention.

An example of a device according to the invention is represented in FIGS. 1 and 2. These figures show a mobile gantry 10 equipped with driving means 30 suitable for driving the gantry in displacement along a stiffener, not represented in these figures but schematically represented by the arrow R. In the invention, the gantry 10 is a support in the form of an inverted U comprising two lateral legs 11, 12 and a bridge 13 linking the two legs 11 and 12. The legs 11 and 12 are placed on either side of the stiffener to be checked. The bridge 13 is situated at a height greater than the height of the stiffener. Preferably, a gap of several centimeters is provided between the web of the stiffener and the bridge 13 to ensure that the inspection device of the invention can be adapted to all kinds of stiffeners.

Figure 3A:
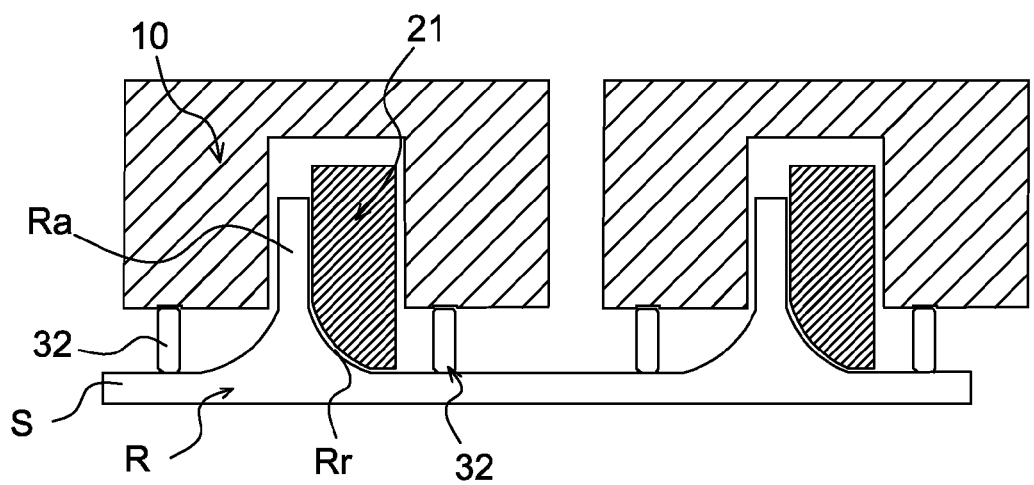
FIGS. 3A and 3B represent simplified schematic views of the device of FIGS. 1 and 2 mounted on a stiffener.

The driving means 30 comprise a motor 31 linked electrically to at least one driving wheel 32. This driving wheel 32 is housed in a module 33 secured to the gantry 10. This module 33 forms a central leg of said gantry. The driving wheel 32, shown notably in FIG. 3A, is mounted parallel to the stiffener R and drives all of the gantry 10. The driving wheel 32 is driven in rotation by the motor 31.

A number of driving wheels 32 can be mounted on the module 33 to ensure an even displacement of the gantry along the stiffener. In this case, the motor 31 drives each of the driving wheels.

The driving wheel or wheels 32 can be made of an adherent material such as elastomer to allow for an adhesion of the gantry onto the surface of the stiffener, facilitating the driving of the gantry 10. Wheels 34, secured to the gantry 10, make it possible to keep the device on the surface S of the structure. In this way, the device of the invention can be used on surfaces which are not necessarily horizontal. It can be used, for example, on surfaces of structures forming an angle of 45° or even of 90° relative to the horizontal. It will thus be understood that the inspection device of the invention allows for a considerable time saving when inspecting stiffeners of incurved or closed structures since the stiffeners can be checked without displacing the structure, regardless of the placement of the stiffener on this structure.

The gantry 10 is equipped also with a protection enclosure 20 inside which is installed the ultrasound sensor 21 and gripping means 40 ensuring that the ultrasound sensor 21 is kept pressed against the stiffener R.

In effect, for the ultrasound sensor 21 to operate optimally, it is important for it to be mechanically pressed against the stiffener R. For this, the gripping means 40 comprise a wall skid 41 having a planar front face 41b and parallel to the surface of the stiffener R. The wall skid 41 has its front face 41b aligned with a front face of the ultrasound sensor. The gripping means further comprise a pressure spring 42 mounted on the rear face 41a (opposite the front face 41b) of the wall skid 41. This spring 42 is suitable for thrusting the wall skid 41 against the stiffener in order to ensure a mechanical contact between said skid and said stiffener regardless of the surface condition of the stiffener. The wall skid 41 also comprises at least one roller 43 mounted in a housing situated on the front face 41b. This roller 43, mounted so as to protrude slightly from its housing, is designed to be in contact with the stiffener and roll over the surface to be checked of said stiffener.

The protection enclosure 20 containing the ultrasound sensor 21 is mounted secured to the wall skid 41. Since the wall skid 41 is fixed longitudinally but mobile transversely relative to the gantry 10, the ultrasound sensor 21 is kept at a distance from the surface of the stiffener R that is always identical. Thus, regardless of any surface defects of the stiffener (groove, roughness, boss, etc.), the ultrasound sensor 21 picks up information of a quality that is always optimal.

It will be understood from the above that, to perform an inspection, the inspection device is positioned around the stiffener R so that the stiffener R is installed between, on the one hand, the module 33 and, on the other hand, the assembly formed by the protection enclosure 20 and the wall skid 41. Since the module 33 is secured to the gantry 10, it drives said gantry in displacement along the stiffener. On the other side of the stiffener relative to the module 33, there are the protection enclosure 20 with the ultrasound sensor 21 and the wall skid 41. The protection enclosure with the ultrasound sensor is driven in displacement by the module 33. Thus, the surface of the stiffener situated facing the protection enclosure 20 and the wall skid 41 can be checked as said protection enclosure is displaced with the ultrasound sensor.

According to the invention, the gantry also supports locating means installed in the module 33. These locating means make it possible to associate a code with each position of the surface of the stiffener in order for the operator to be able to locate any stiffener defects. These locating means comprise, for example, a coding wheel, or coder, suitable for determining the position of the ultrasound sensor as it is displaced. They thus make it possible to synchronize each defect of the stiffener with a location of the area in which this defect is situated. In this way, the inspection device of the invention generates a mapping of the stiffener (including the hypothetical defects). The operator, on reading this mapping, can determine whether the state of material health of the stiffener is satisfactory or not.

In a variant of the invention, the inspection device comprises end-of-trajectory detection means linked to the driving means to automatically stop the displacement of the gantry at the end of the stiffener. These end-of-trajectory detection means can comprise one or more end-of-travel detector(s) 80. This end-of-travel detector, installed for example under the bridge 13 of the gantry, at the level of the wall skid 41, is suitable for detecting the presence or the absence of stiffener. As soon as it detects the absence of stiffener, it sends a signal to the driving means. On receiving this signal, the motor 31 ceases driving the driving wheel, which causes the displacement of the gantry 10 to be stopped.

In one embodiment of the invention, the gantry 10 is equipped with clamps 60 linked to the protection enclosure 20 (as is the case in FIG. 2) and to the gripping means 40. These clamps 60, with their sliding bolt 61, make it possible to separate the protection enclosure and the wall skid from the module 33 for the stiffener R to be able to be positioned between these elements in the manner explained previously. These clamps 60 and the gripping means 40 make it possible to adapt the inspection device to all kinds of stiffeners with all kinds of thicknesses.

It is known that, to have optimal efficiency, the ultrasound sensor requires a coupling medium, generally water, making it possible to propagate the ultrasounds. For this, in the invention, provision is made for a film of water to be applied along the surface of the stiffener. This film of water can be obtained by a water intake situated above the ultrasound sensor. In this case, the protection enclosure 20 comprises a water tank placed between the ultrasound sensor 21 and the bridge 13 of the gantry. An opening at the bottom of the tank allows the water to flow along the surface of the stiffener, in front of the ultrasound sensor.

Figure 3B:
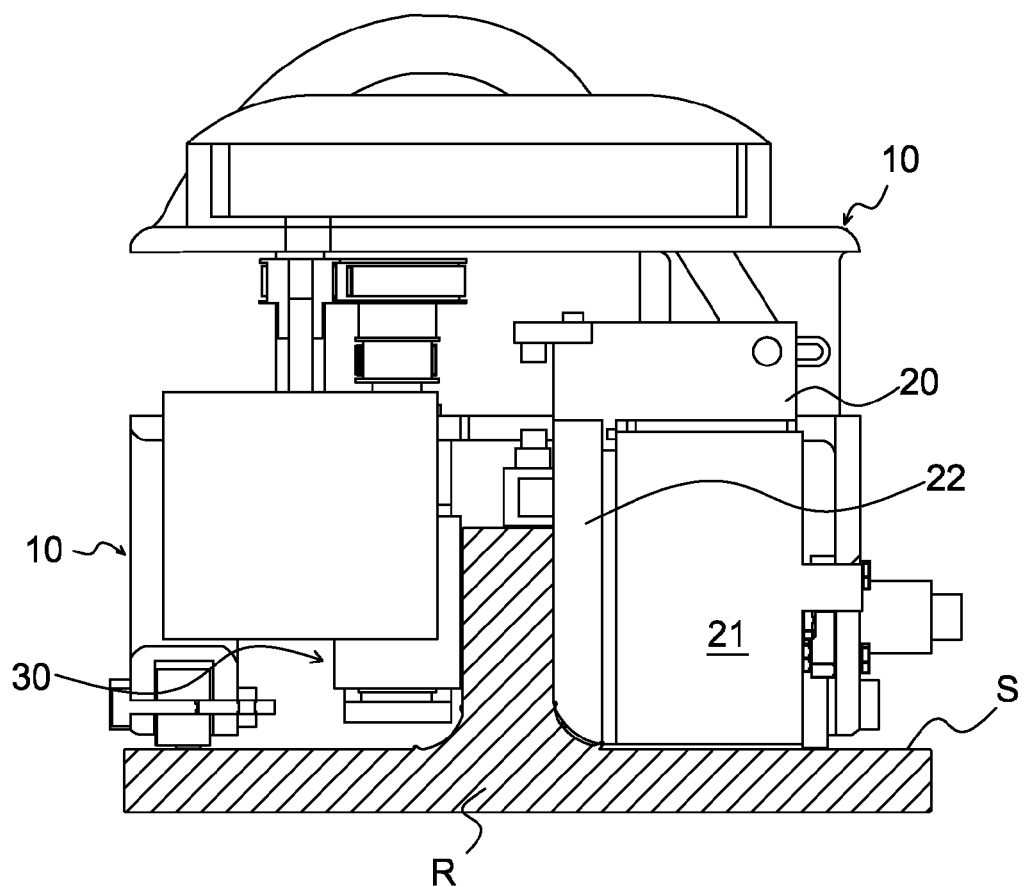

The film of water can be obtained by a water column 22, as shown in FIG. 3B, placed between the ultrasound sensor 21 and the stiffener R.

The film of water can be obtained also by a spray device installed in the protection enclosure, above the ultrasound sensor. Such a spray device makes it possible to spray droplets of water onto the surface of the stiffener to be checked.

The supply of water to the inspection device of the invention is provided by means of a pipe (not represented in the figures), for example made of silicone, linking the water tank or the spray device to a remote water supply source.

According to the invention, the ultrasound sensor is installed in the protection enclosure 20, facing the surface of the stiffener to be checked. This ultrasound sensor 21 is suitable for supplying measurements relating to each area of the surface of the stiffener. It is therefore suitable for supplying measurements relating to the web of the stiffener, that is to say the rectilinear wall of the stiffener (wall substantially at right angles to the surface of the structure on which the stiffener is mounted), but also to the radius of the stiffener, that is to say the rounded part of the stiffener which links the web and the surface of the structure. FIGS. 3A and 3B show, in a highly schematic way, an exemplary stiffener R mounted on a structure S. The stiffener R comprises a web Ra and a radius Rr. The inspection device 1 is represented schematically by the gantry 10 (which here incorporates the motor 31, the module 33, the gripping means 40, the end-of-trajectory detection means 80), the ultrasound sensor 21 and the driving wheels 32. The ultrasound sensor 21 can be chosen according to the type of stiffener to be checked. For example, for a T-shaped stiffener, as shown in FIGS. 3A and 3B, the enclosure of the ultrasound sensor 21 has a rounded form enabling it to be in contact both with the radius Rr and the web Ra of said stiffener R. The ultrasound sensor has a form which enables it to perfectly follow the form of the stiffener. Other types of ultrasound sensors can of course be mounted in the inspection device of the invention to ensure the contact with the stiffener.

Once mounted in the protection enclosure, the ultrasound sensor can be protected, notably from splashes of water, by a watertight wall positioned on the rear face of said sensor.

Figure 4:
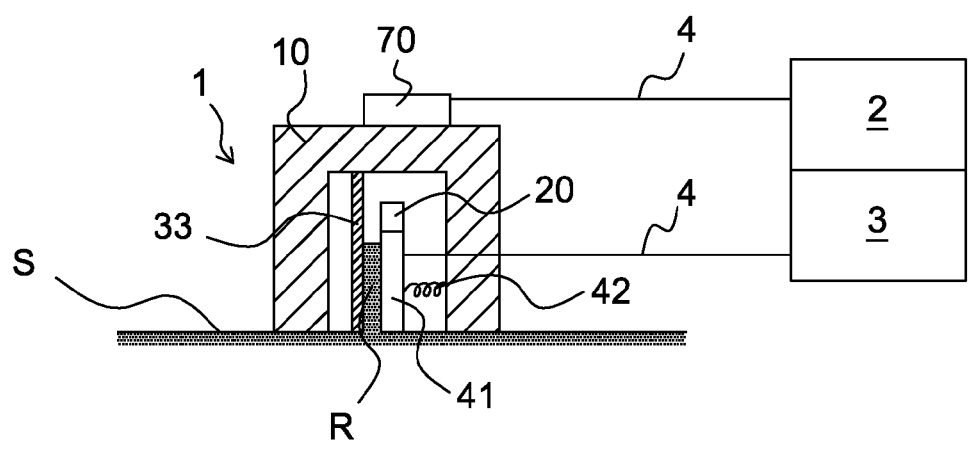
FIG. 4 represents a schematic view of the inspection system of the invention.

As can be seen in FIG. 2, the bridge 13 of the gantry 10 is equipped with an electrical connection interface 70. This connection interface 70 comprises electrical cable outlets making it possible to electrically link the inspection device to a remote control device and remote display device. In FIG. 4, the control device 1 which has just been described has been represented with its electrical wiring 4. This electrical wiring 4 can run along the gantry 10, without risk, since the gantry is displaced only longitudinally along the stiffener, but never transversely. However, a variant of the invention provides for furnishing the electrical cables 4 with an automatic winding device which makes it possible to unwind the cables when the gantry advances and wind the cables when the gantry moves back.

These electrical cables 4 are linked, on the one hand, to a display device 3 on which an operator can view the measurements from the ultrasound sensor and, on the other hand, to a control device 2. The control device 2 enables the operator to control the displacement, forward or backward, of the control device 1. In effect, even if the inspection device 1 of the invention is designed to operate in one direction (called forward direction), it can be made also to move back, for example to be recovered by the operator once the checking of the stiffener has been performed.

The display device 3 ensures the acquisition of the signal measured by the ultrasound sensor and the display of the duly acquired mapping. It thus enables the operator to view and analyze, remotely, the state of internal health of the stiffener according to the mapping.

Obviously, the control device 2 and the display device 3 can be combined in one and the same machine.

According to a variant of the invention, the data measured by the ultrasound sensor are recorded, which enables a same operator to check the state of a plurality of stiffeners inspected simultaneously by a plurality of inspection devices. It is in fact possible to arrange a plurality of inspection devices, in parallel, around a plurality of stiffeners (as shown in FIG. 3A) in order to reduce the overall time to inspect a structure. It is also possible, to reduce the labor costs, to entrust the placement of a plurality of inspection devices to an unqualified operator and the checking of all the mappings obtained by these inspection devices to a qualified operator.

The inspection device which has just been described has dimensions of the order of 200 $mm^3$ and a weight of approximately 2 kg. It is therefore easy to handle and to install around a stiffener, even when the stiffener is difficult to access, for example in a closed structure. Because of its small bulk, it can be installed around all the stiffeners, regardless of the separation between two stiffeners. Furthermore, its gripping means make it possible not only for it to be adapted to all the stiffener thicknesses, but also to inspect all the stiffeners of a structure, even when the structure is not planar.

Furthermore, its small bulk and its autonomy allow for a use in maintenance, in addition to a use after production.

The invention claimed is:

1. An inspection device for inspecting a stiffener of a structure made of composite materials of an aircraft, comprising:
    at least one ultrasound sensor configured to supply measurements relating to an internal health state of the stiffener;
    an ultrasound sensor protection enclosure to house said at least one ultrasound sensor;
    a mobile gantry configured to be displaced along the stiffener and to mount the protection enclosure with said at least one ultrasound sensor inside, the mobile gantry is in a form of an inverted U and comprises two lateral legs placed on either side of the stiffener,
    a driver configured to drive the mobile gantry along the stiffener, the driver is housed in a module secured to the mobile gantry and forms a central leg of the mobile gantry;
    a gripper secured to the protection enclosure and configured to keep said at least one ultrasound sensor pressed against a surface of the stiffener to be inspected; and
    a locator to synchronize each area of the surface of the stiffener with the measurements of said at least one ultrasound sensor.

2. The inspection device as claimed in claim 1, wherein the gripper comprises:
    at least one pressure spring;
    a wall skid having a front face aligned with a front face of said at least one ultrasound sensor and a rear face to bear said at least one pressure spring; and
    at least one roller housed in the front face of the wall skid and configured to roll over the surface of the stiffener to ensure a mechanical contact between the wall skid and the stiffener.

3. The inspection device as claimed in claim 1, wherein the protection enclosure comprises a water tank configured to maintain a film of water between the said at least one ultrasound sensor and the surface of the stiffener.

4. The inspection device as claimed in claim 1, wherein the driver comprises a motor linked electrically to at least one driving wheel configured to displace the mobile gantry.

5. The inspection device as claimed in claim 4, wherein said at least one driving wheel is housed in the module secured to the mobile gantry and forms the central leg of the mobile gantry.

6. The inspection device as claimed in claim 5, wherein the module is situated facing the protection enclosure of said at least one ultrasound sensor, along a surface opposite the surface of the stiffener to be inspected.

7. The inspection device as claimed in claim 1, wherein the mobile gantry further comprises a bridge linking the two lateral legs.

8. The inspection device as claimed in claim 1, wherein the locator comprises a coder configured to determine a position of said at least one ultrasound sensor as it is displaced.

9. The inspection device as claimed in claim 1, further comprising an end-of-trajectory detector linked to the driver to automatically stop displacement of the mobile gantry at an end of the stiffener.

10. The inspection device as claimed in claim 1, wherein the protection enclosure of said at least one ultrasound sensor has a form following a form of the stiffener.

11. A system for inspecting a stiffener of a structure made of composite materials of an aircraft, comprising:
    the inspection device as claimed in claim 1;
    a control device linked to the inspection device; and
    a display device configured to display the measurements from said at least one ultrasound sensor, the display device is linked to the inspection device.

* * * * *